United States Patent [19]

Haining

[11] Patent Number: 5,019,049

[45] Date of Patent: May 28, 1991

[54] INTRAVENOUS CATHETER AND INSERTION DEVICE

[76] Inventor: Michael L. Haining, 6731 Ashmore, Houston, Tex. 77069

[21] Appl. No.: 482,014

[22] Filed: Feb. 20, 1990

[51] Int. Cl.$^5$ .............................................. A61M 5/178
[52] U.S. Cl. ..................... 604/165; 604/198
[58] Field of Search .................. 604/110, 164–170, 604/198, 263

[56] References Cited

U.S. PATENT DOCUMENTS

| | | | |
|---|---|---|---|
| 3,595,230 | 7/1971 | Suyeoka et al. | 604/164 |
| 4,170,993 | 10/1979 | Alvarez | 604/263 X |
| 4,832,696 | 5/1989 | Luther et al. | 604/164 |
| 4,850,961 | 7/1989 | Wanderer et al. | 604/53 |
| 4,850,968 | 7/1989 | Romano | 604/110 |
| 4,909,793 | 3/1990 | Vining et al. | 604/164 |
| 4,944,725 | 7/1990 | McDonald | 604/164 |
| 4,944,728 | 7/1990 | Carrell et al. | 604/164 |
| 4,950,252 | 8/1990 | Luther et al. | 604/198 |

Primary Examiner—John D. Yasko
Assistant Examiner—Adam J. Cermak
Attorney, Agent, or Firm—Richard L. Moseley

[57] ABSTRACT

To protect against accidental needle prick a catheter and insertion device are provided wherein the needle is retractable within the device after insertion of the catheter. The device comprises a hollow barrel or tube of semi-rigid plastic material into which the needle can be retracted after use. The insertion needle is mounted on a carrier with the sharp end oriented toward an open insertion end of the barrel with the catheter snugly fit about the needle. A sliding tab is mounted to the carrier by an outwardly biased flexible member and extends through a longitudinal slot in the barrel. Near either end of the slot V notches are provided in the internal wall of the barrel to engage locking hubs on the sliding tab to releasably lock the carrier in either the exposed or retracted position. A flat catheter locking surface is provided at the insertion of the barrel with a reverse slope to allow the catheter flange to slide onto the flat surface and allow easy retraction of the needle without disturbing the inserted catheter.

3 Claims, 1 Drawing Sheet

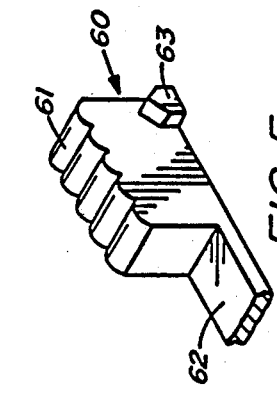
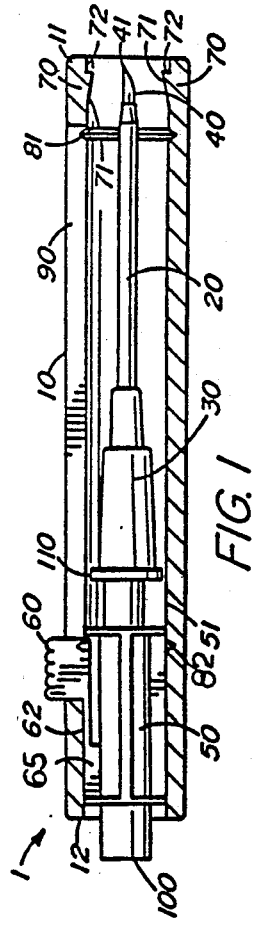
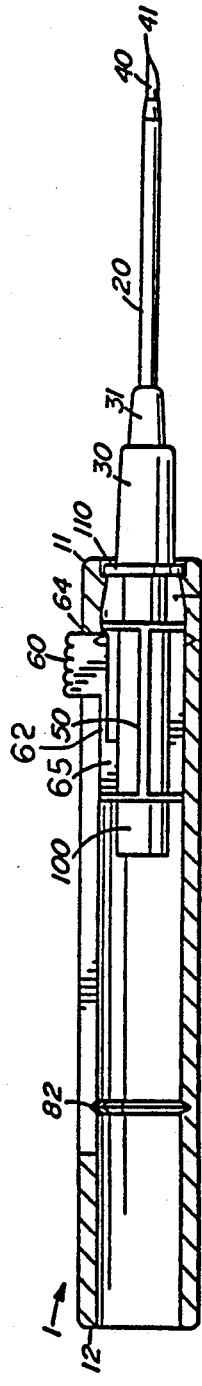
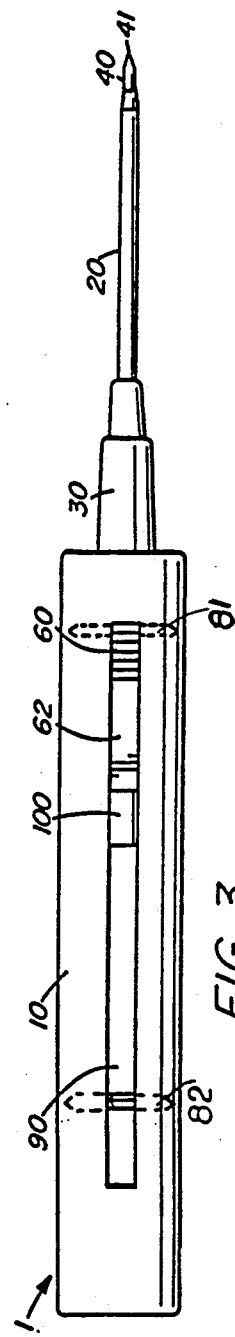
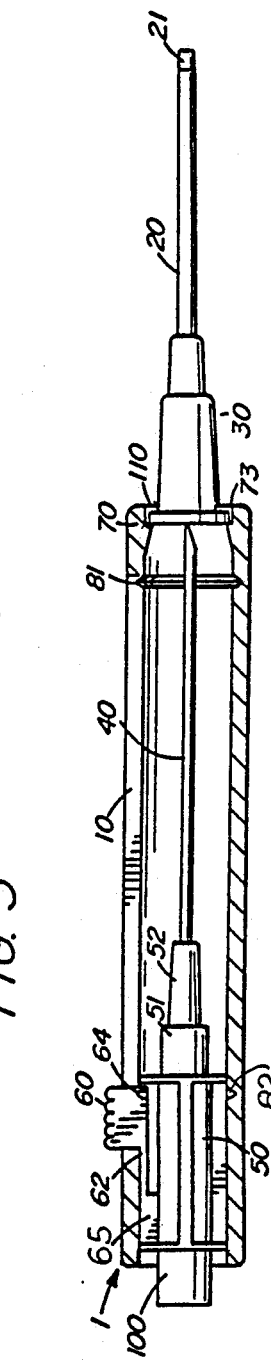

INTRAVENOUS CATHETER AND INSERTION DEVICE

BACKGROUND OF THE INVENTION

1. Field of the Invention

The present invention relates to a device for the insertion of a flexible catheter into a vein of a patient for intravenous administration of fluids. More particularly the invention relates to devices wherein the flexible catheter is inserted into the vein by a sharp needle about which the catheter is snugly mounted, and the needle and catheter are inserted into the vein and the needle removed leaving the catheter in place. Most particularly the invention relates to a catheter insertion device wherein the insertion needle is retractable into the device after removal to protect the user from accidental needle prick.

2. Related Art

The development of flexible intravenous catheters has greatly increased the comfort of patients during intravenous administration of medicinal fluids. The flexible catheter also prevents unwanted puncture of the vein. The flexible catheter normally consists of a narrow tube of nylon or teflon construction with a rigid member attached at the rear end for connection to the source of fluid to be administered intravenously.

Because the catheter is flexible it cannot by itself be inserted into the vein. Therefore, the catheter is snugly nested about a sharp needle which can be inserted into the vein. After insertion the sharp needle is withdrawn leaving the catheter in place for connection to the fluid source. The insertion needle is simply discarded as it is intended for a single use only. Often the needle is discarded in a careless manner leaving the exposed needle point as a hazard.

Accidental needle prick has been a problem for years in the health care industry. However, the recent advent of the HIV or AIDS virus has focused attention on the problem. While several diseases, such as viral hepatitis, may be contracted from bodily fluids of infected persons, HIV has caused the most concern because to date no preventative or cure is known. Protection against accidental needle is expected to remain a concern even after a vaccine or cure is found, an ounce of prevention always being worth a pound of cure.

SUMMARY OF THE INVENTION

To protect against accidental needle prick a catheter and insertion device are provided wherein the needle is retractable within the device after insertion of the catheter. The device comprises a hollow barrel or tube of semi-rigid plastic material into which the needle can be retracted after use. The insertion needle is mounted on a carrier with the sharp end oriented toward an open insertion end of the barrel with the catheter snugly fit about the needle. A sliding tab is mounted to the carrier by an outwardly biased flexible member and extends through a longitudinal slot in the barrel. Near either end of the slot V notches are provided in the internal wall of the barrel to engage locking hubs on the sliding tab to releasably lock the carrier in either the exposed or retracted position. A flat catheter locking surface is provided at the insertion of the barrel with a reverse slope to allow the catheter flange to slide onto the flat surface and allow easy retraction of the needle without disturbing the inserted catheter.

BRIEF DESCRIPTION OF THE DRAWING

FIG. 1 is a side elevational view in cross section showing the catheter insertion device with the needle and catheter in the retracted position.

FIG. 2 is a side elevational view in cross section showing the needle and catheter in the exposed position.

FIG. 3 is a top view of the catheter insertion device with the needle and catheter in the exposed position.

FIG. 4 is a side elevational in cross section showing the needle retracted from the catheter.

FIG. 5 is a perspective view of the sliding tab showing one of the locking hubs for locking the carrier in the exposed or retracted position.

DESCRIPTION OF THE PREFERRED EMBODIMENT

For a detailed description of the preferred embodiment the reader is referred to the appended figures in which like components are given like numerals for ease of reference.

The figures generally show a catheter insertion device 1 having a hollow cylindrical barrel 10 of semi-rigid plastic material. For orientation purposes only, the barrel 10 is defined as having an insertion end 11 and a distal end 12. A flexible catheter 20 is snugly fit about an insertion needle 40 and both mounted on a carrier 50 which slidably mounted within the barrel 10. In FIG. 1 the device is depicted as proposed to be shipped with the carrier 50, needle 40 and catheter 20 withdrawn into barrel 10. Shipment will be in a sterile package (not shown). In this configuration no protective sheath about the needle 40 and catheter 20 would be required because they are encased by the barrel 10.

In FIG. 2 the device is depicted with the needle 40 and catheter 20 exposed for insertion into the vein of the patient. FIG. 3 is an overall depiction with the device rotated 90° about its longitudinal axis clearly showing the sliding slot 90 in the barrel 10. FIG. 4 depicts the device with the needle 40 retracted into the barrel 10 leaving the catheter 20 in place. FIG. 5 depicts the sliding tab 60 in enlarged detail.

Referring now in particular to the barrel 10 as depicted in FIGS. 1-4, it is shown to have a longitudinal slot 90 partially extending between the two ends 11 and 12. Near either end of the slot are circumferential V notches 81 and 82 as shown. Additionally, at the insertion end there is provided an inwardly projecting circumferential shoulder 70 having a rear surface 71 sloped radially outwardly toward the distal end 12 and a flat surface 72 facing the insertion end 11.

The needle carrier 50 is slidably mounted with the barrel 10 having the sliding tab 60 mounted thereto by base 65 and flexible member 62 biasing the tab outward to extend through slot 90. Referring now to FIG. 5 the tab 60 is shown to have V topped hubs 63 and 64 on either side (only one shown in FIG. 5). As member 62 biases tab outward V topped hubs 63 and 64 are forced into releasable locking engagement with either of V shaped notches 81 or 82.

As may be more easily seen in FIG. 4 the insertion needle 40 is mounted to the carrier 50 by mounting post 51 which includes a forward projecting frusto-conical section 52. Normally the longitudinal axis of the needle will be aligned with the longitudinal axis of the barrel. The flexible catheter 20 is mounted snugly about the insertion needle 40 with the sharp point 41 of needle extending from the catheter end 21. Catheter 20 includes a hollow base having two frusto-conical sections 30 and 31. In particular frusto-conical section 31 is nested over needle base section 52. At the rear or distal end of catheter base 30 a circumferential flange 110 extends outward the outer diameter of which is slightly greater than the inner diameter of barrel shoulder 70.

In use, the catheter and insertion device are removed from their sterile packaging with the needle carrier 50, needle 40 and catheter 20 in the retracted position, the carrier 20 being locked into the retracted position by engagement of the V topped hubs 63 and 64 with rear V notch 82. The user presses down (or inwardly) on tab 60 against the biasing pressure of flexible member to release the hubs 63 and 64 from the rear notch 82 and slides the carrier 50 with needle 40 and catheter 20 forward toward the insertion end. The flange 110 passes over the sloped surface 71 and engages the flat surface 72 at the same time as the hubs 63 and 64 engage the front notch 81. The catheter may then be inserted into the patient's vein. The user again presses downward on the tab 60 to release the hubs 63 and 64 from the front V notch 81 and slides the carrier and needle toward the distal end, the engagement of the flange 110 against the flat surface 72 prevents the catheter 20 from also being retracted leaving it in place. The needle is locked into the retracted position by the biasing force of flexible member 62 and may be safely discarded with the needle 40 encased by the barrel 10. A small clearance 73 between flange 110 and shoulder 70 prevents the catheter 20 from sticking within the end 11 of barrel 10. Alternatively, the insertion device may be withdrawn with the needle 40 exposed and then the needle 40 retracted.

The invention claimed is:

1. An intravenous catheter insertion device comprising:
   (a) a hollow cylindrical barrel of semi-rigid plastic material having an insertion end and a distal end;
   (b) a catheter insertion needle carrier slidably mounted within said barrel;
   (c) a catheter insertion needle fixedly attached to said needle carrier and oriented toward said insertion end;
   (d) an intravenous catheter removably secured about said needle, said intravenous catheter comprising a rigid hollow conical base and a flexible hollow tube extending from the narrow end of said base, said base having a circumferential flange extending about the wide end;
   (e) sliding means mounted on said needle carrier extending exterior of said barrel for sliding said needle carrier with said needle and said catheter within said barrel to expose or retract said needle with said catheter; and
   (f) a locking surface at said insertion end having an inner diameter slightly smaller than the outer diameter of said circumferential flange to prevent retraction of said catheter after exposure.

2. An intravenous catheter insertion device comprising:
   (a) a hollow cylindrical barrel of semi-rigid plastic material having an insertion end and a distal end, said barrel including
      (1) a longitudinal slot partially extending between said ends,
      (2) an inwardly projecting locking surface near said insertion end, and
      (3) internal locking notches near either end;
   (b) a catheter insertion needle carrier slidably mounted within said barrel;
   (c) a rigid sliding member extending through said slot and fixedly attached to said needle carrier by an outwardly biased flexible member, said flexible member having a locking ridge on one side that is releasably locked into either of said locking notches by said biased member;
   (d) a catheter insertion needle mounted on said needle carrier and oriented toward said insertion end; and
   (e) an intravenous catheter removably secured about said needle, said catheter having a locking flange at the distal end which has a slightly larger outer diameter than the inner diameter of said locking surface.

3. An intravenous catheter insertion device comprising:
   (a) a hollow cylindrical barrel of having an insertion end and a distal end, said barrel including
      (1) a longitudinal slot partially extending between said ends, and
      (2) internal locking notches near either end;
   (b) a catheter insertion needle carrier slidably mounted within said barrel;
   (c) a rigid sliding member extending through said slot and fixedly attached to said needle carrier by an outwardly biased flexible member, said flexible member having a locking ridge on one side that is releasably locked into either of said locking notches by said biased member;
   (d) a catheter insertion needle mounted on said needle carrier and oriented toward said insertion end; and
   (e) an intravenous catheter removably secured about said needle.

* * * * *